(12) United States Patent
Fenster et al.

(10) Patent No.: US 12,318,251 B2
(45) Date of Patent: Jun. 3, 2025

(54) ACTUATOR FOR ULTRASOUND TRANSDUCER

(71) Applicant: Centre for Imaging Technology Commercialization (CIMTEC), London (CA)

(72) Inventors: Aaron Fenster, London (CA); Kevin Barker, Lucan (CA)

(73) Assignee: Centre for Imaging Technology Commercialization (CIMTEC), London (CA)

( * ) Notice: Subject to any disclaimer, the term of this patent is extended or adjusted under 35 U.S.C. 154(b) by 561 days.

(21) Appl. No.: 17/692,372

(22) Filed: Mar. 11, 2022

(65) Prior Publication Data

US 2022/0287677 A1 Sep. 15, 2022

Related U.S. Application Data

(60) Provisional application No. 63/159,518, filed on Mar. 11, 2021.

(51) Int. Cl.
*A61B 8/00* (2006.01)
(52) U.S. Cl.
CPC .......... *A61B 8/4218* (2013.01); *A61B 8/4461* (2013.01); *A61B 8/483* (2013.01)
(58) Field of Classification Search
CPC ...... A61B 8/4218; A61B 8/4461; A61B 8/483
See application file for complete search history.

(56) References Cited

U.S. PATENT DOCUMENTS

| 5,562,095 | A | 10/1996 | Downey et al. | |
|---|---|---|---|---|
| 10,052,083 | B2 | 8/2018 | Barker et al. | |
| 2005/0256402 | A1* | 11/2005 | Kawashima | A61B 8/14 600/437 |
| 2010/0125207 | A1* | 5/2010 | Kim | G01S 15/8938 600/459 |
| 2014/0121520 | A1* | 5/2014 | Wang | A61B 8/403 600/444 |
| 2015/0018685 | A1* | 1/2015 | Barker | A61B 8/4218 600/459 |
| 2022/0211320 | A1* | 7/2022 | Ha | A61N 5/0616 |

* cited by examiner

*Primary Examiner* — Jeffrey G Hoekstra
*Assistant Examiner* — Adam D. Kolkin
(74) *Attorney, Agent, or Firm* — Brunet & Co. Ltd.; Robert Brunet; Hans Koenig

(57) ABSTRACT

An actuator for moving an ultrasound transducer has a main body configured to be positioned adjacent to a target region of interest to be examined; and, a motor mounted on the main body. The motor is configured to have an ultrasound transducer connected thereto to simultaneously translate and rotate the ultrasound transducer to perform a compound scan of the target region of interest when the ultrasound transducer is connected to the motor. An ultrasound device has an ultrasound transducer movably mounted on the actuator. The actuator requires only single motor to effect both translation and rotation of the transducer thereby simplifying operation and providing a more compact device.

19 Claims, 7 Drawing Sheets

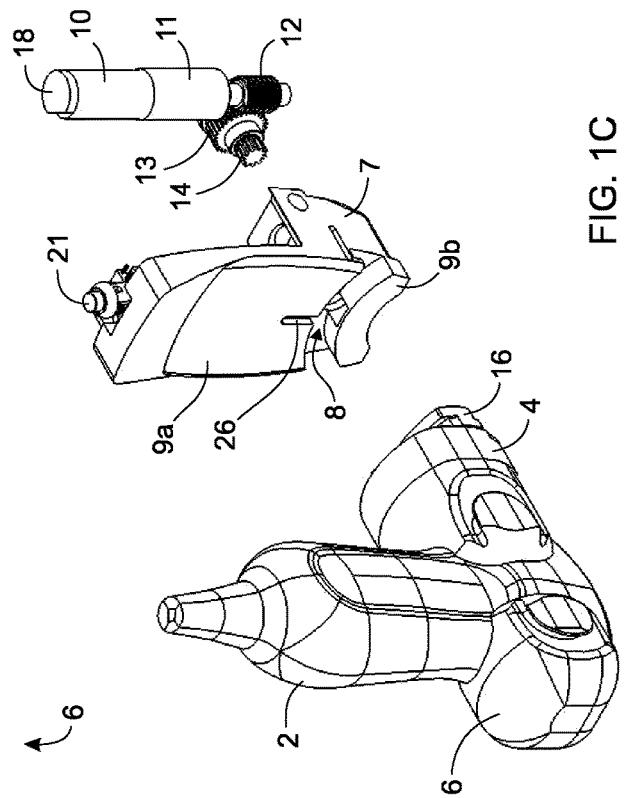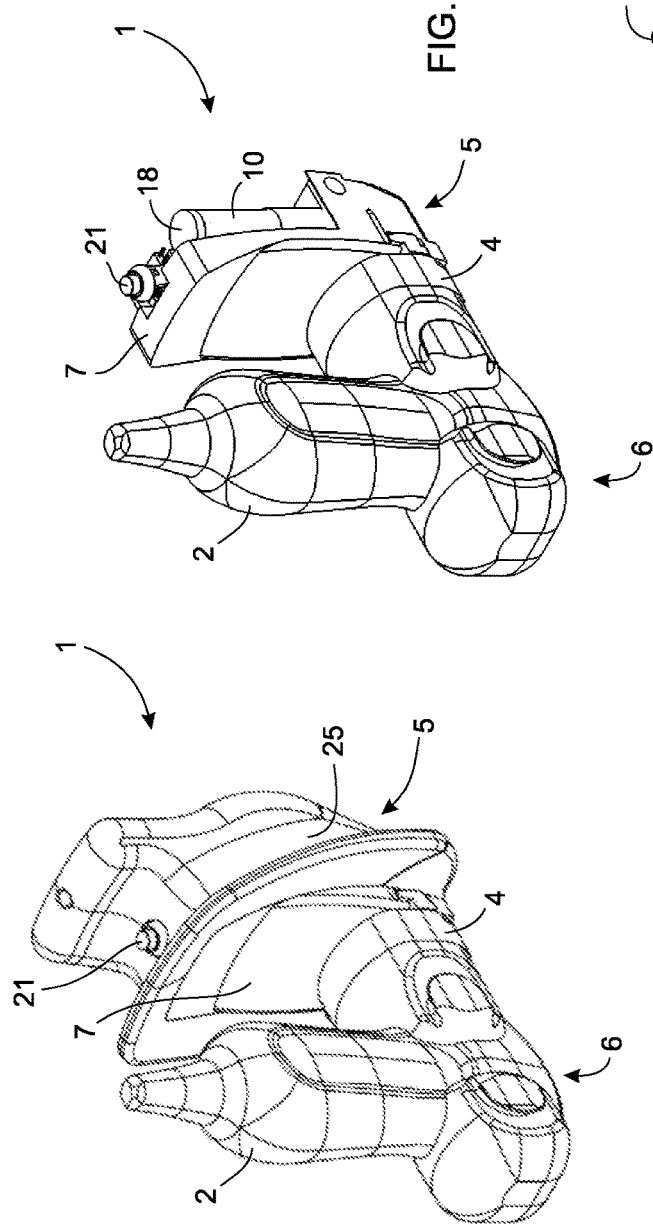
FIG. 1C
FIG. 1B
FIG. 1A

ACTUATOR FOR ULTRASOUND TRANSDUCER

CROSS-REFERENCE TO RELATED APPLICATIONS

This application claims the benefit of U.S. patent application 63/159,518, filed Mar. 11, 2021, which is incorporated herein by reference.

FIELD

This application relates to medical devices and methods, in particular to an actuator for an ultrasound transducer, the actuator capable of moving the ultrasound transducer to perform a compound scan of a target region.

BACKGROUND

A variety of approaches have been developed to produce three-dimensional (3D) ultrasound images using both one-dimensional (1D) ultrasound arrays and two-dimensional (2D) ultrasound arrays. The use of 1D ultrasound arrays to produce 3D ultrasound images requires methods to determine the position and orientation of acquired 2D ultrasound images within the 3D ultrasound image volume. The use of 2D ultrasound arrays to produce 3D ultrasound images requires a 3D scan-converter to build the 3D ultrasound images from the sequence of transmit acoustic signals.

U.S. Pat. No. 5,562,095 to Downey et al. and U.S. Pat. No. 10,052,083 to Barker et al., the entire disclosures of which are incorporated herein by reference, disclose 3D ultrasound imaging systems, in particular for imaging human organs, comprising assemblies onto which ultrasound probes may be mounted, motors, and drives for either rotating or scanning the ultrasound probe relative to the human organ under investigation. The assembly in U.S. Pat. No. 10,052,083 further comprises a second motor for translating the ultrasound probe as well as rotating the probe. U.S. Pat. Nos. 5,562,095 and 10,052,083 also disclose computers for executing software for controlling movement of the assemblies to rotate or scan the ultrasound probes.

Improvements in 3D ultrasound imaging are generally desired. In particular, there is a need for an actuator for moving an ultrasound probe to obtain 3D ultrasound images, the actuator being simpler to operate and having fewer components.

SUMMARY

An actuator for moving an ultrasound transducer, the actuator comprising: a main body configured to be positioned adjacent to a target region of interest to be examined; and, a motor mounted on the main body, the motor configured to have an ultrasound transducer connected thereto to simultaneously translate and rotate the ultrasound transducer to perform a compound scan of the target region of interest when the ultrasound transducer is connected to the motor.

An ultrasound device comprises the actuator described above and an ultrasound transducer connected to the motor of the actuator.

The actuator requires only single motor to effect both translation and rotation of the ultrasound transducer thereby simplifying operation and providing a more compact device while being able to acquire 3D ultrasound images.

In some embodiments, the actuator further comprises a drive block to which the ultrasound transducer is mounted. The drive block is operatively connected to the motor to be rotationally and translationally moved by the motor. In some embodiments, the motor is operatively connected to a rotatable engagement structure that is rotationally driven by the motor. In some embodiments, the drive block comprises an arcuate engagement surface that is engaged with the rotatable engagement structure. Rotation of the rotatable engagement structure drives the arcuate engagement surface thereby causing the drive block to both rotate with the rotatable engagement structure and translate laterally relative to a rotation axis of the rotatable engagement structure. The drive block rotates about a point that is a center of a circle of which the arcuate engagement surface is a part. The drive block translates along a perimeter of the circle. In some embodiments, the rotatable engagement structure comprises a toothed gear (e.g., a pinion gear). In some embodiments, the arcuate engagement surface comprises a toothed track (e.g., a segment of an internal ring gear) that engages with the toothed gear.

In some embodiments, the main body comprises an arcuate channel. In some embodiments, drive block comprising the arcuate engagement surface has a complementary shape to the arcuate channel so that the portion of the drive block with the arcuate engagement surface can be housed in the arcuate channel while permitting the drive block to rotate and translate when driven by the motor.

In some embodiments, the actuator further comprises an encoder for determining position of the drive block as the drive block rotates and translates. In some embodiments, the encoder determines the rotational position of a rotating part of the motor, and the position of the drive block is derived from the rotational position of the rotating part of the motor.

In some embodiments, the actuator further comprises a sensor (e.g., a limit switch) for stopping the motor at an end of the compound scan.

In some embodiments, the actuator further comprises a casing for the main body enclosing at least the motor. In some embodiments, the actuator further comprises a user actuatable control on the main body to start the compound scan. In some embodiments, the actuator is configured to be mounted on a robot arm and controlled by a programmed logic circuit.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which:

FIG. 1A depicts a perspective view of an ultrasound device comprising an ultrasound transducer mounted on an actuator for moving the ultrasound transducer.

FIG. 1B depicts the device of FIG. 1A with a casing removed from a main body of the actuator.

FIG. 1C depicts an exploded view of the device depicted in FIG. 1B.

DETAILED DESCRIPTION

Figure 2C:
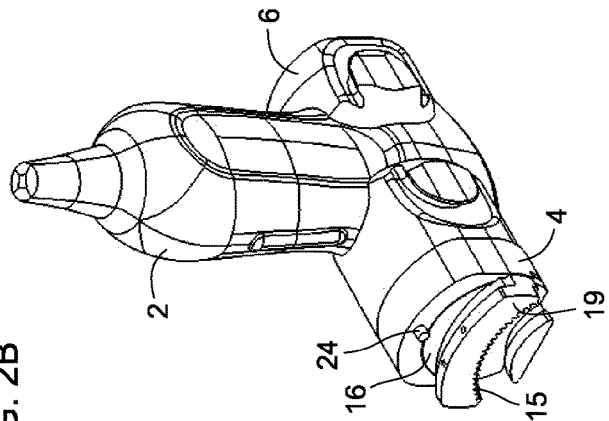
FIG. 2C depicts an exploded view of the device depicted in FIG. 2B.
Figure 2B:
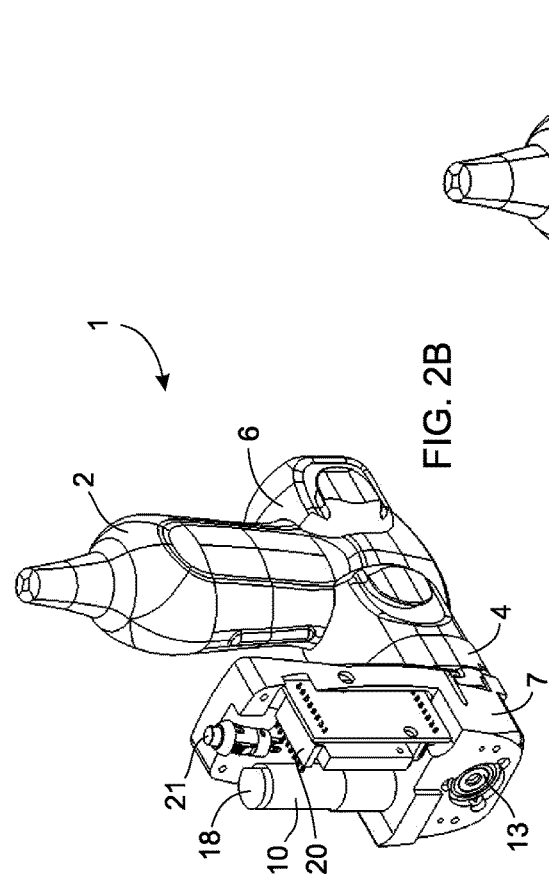
FIG. 2B depicts the device of FIG. 2A with the casing removed from the main body of the actuator.
Figure 2A:
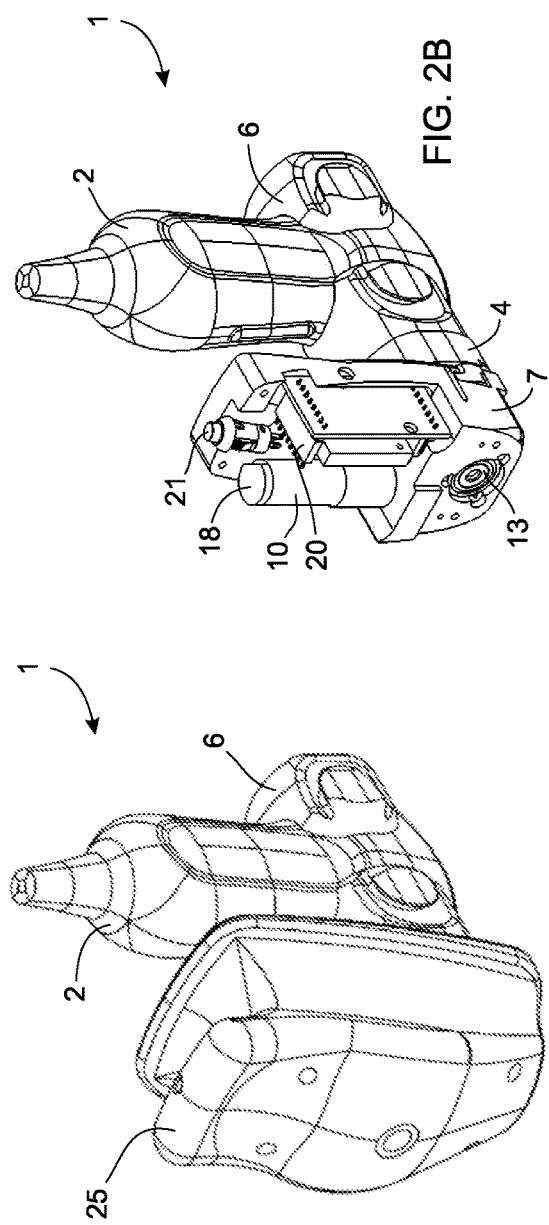
FIG. 2A depicts a perspective view of the device of FIG. 1A from a different perspective.
Figure 3B:
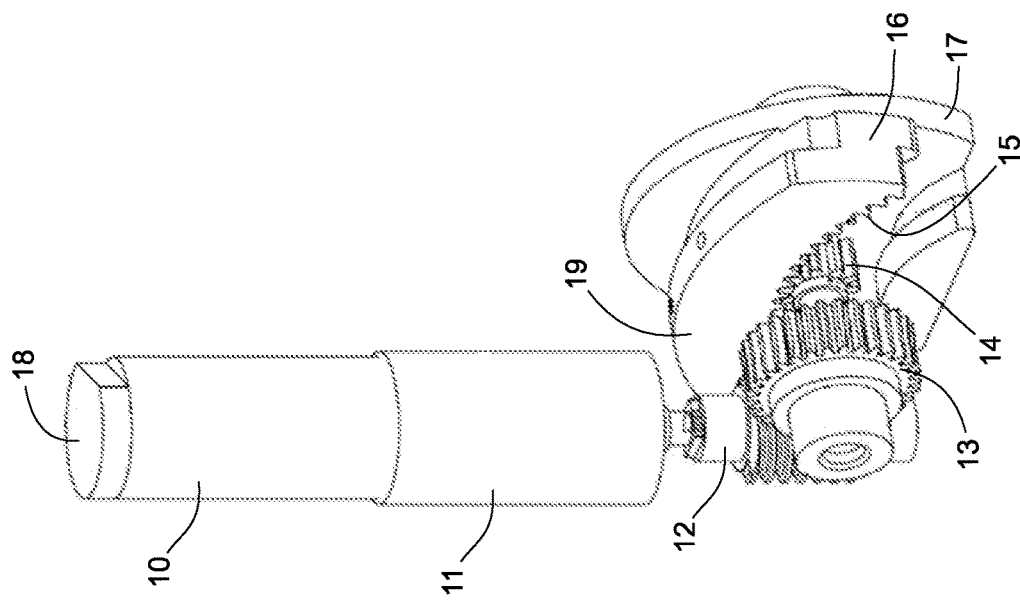
FIG. 3B depicts how a motor mounted on the main body depicted in FIG. 3A is connected to a drive block of the device of FIG. 1A illustrating how the motor is able to move the drive block.
Figure 3A:
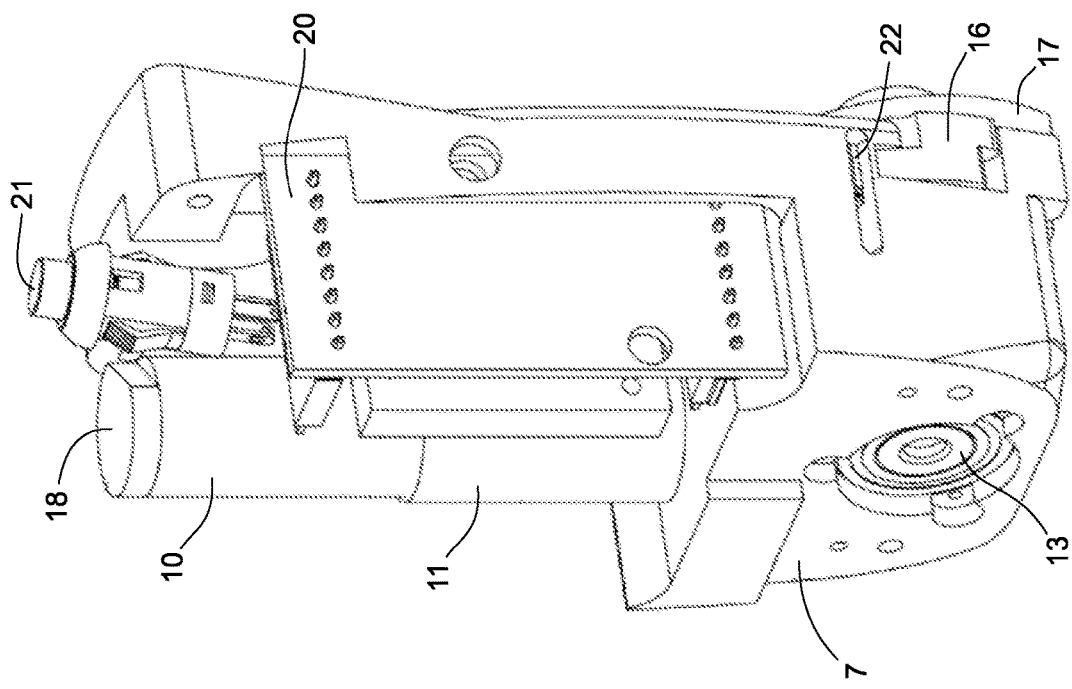
FIG. 3A depicts the main body of the device of FIG. 1A.

With reference to FIG. 1A to FIG. 5C, a single motor hybrid ultrasound device 1 is depicted having an actuator 5 with an ultrasound transducer 6 movably mounted thereon. The actuator 5 comprises a main body 7 having a motor 10 (e.g., a brushed DC motor) mounted thereon. Operatively connected to the motor 10 is a drive train operatively connected to the ultrasound transducer 6 for rotating and translating the ultrasound transducer 6 when the motor 10 is operated. In this embodiment, the drive train comprises a set of linked gears. For example, the motor 10 is operatively connected to a planetary gear head 11, which is operatively linked by a shaft to a worm 12, which is meshed with a worm gear 13, which is operatively connected by a shaft to a pinion gear 14, which is engaged with the teeth of an internal ring gear segment 15, which forms part of a drive block 16 of the actuator 5, the drive block 16 having a mounting adapter 17 for mounting the drive block 16 to the ultrasound transducer 6. The ultrasound transducer 6 comprises a corresponding receiver 4 for receiving the mounting adapter 17 of the drive block 16 in order to mount the ultrasound transducer 6 on the drive block 16. The main body 7 comprises an arcuate channel 8 defined by an upper plate 9a and a lower plate 9b of the main body 7. The drive block 16 comprises a curved guide slide 19 having a complementary arcuate shape to the arcuate channel 8 so that the drive block 16 can be inserted into the arcuate channel 8 to be movably mounted therein. The curved guide slide 19 comprises the internal ring gear segment 15 on a lower face of the curved guide slide 19. The pinion gear 14 protrudes into the arcuate channel 8 where teeth of the pinion gear 14 engage with teeth of the internal ring gear segment 15. Operation of the motor 10 is therefore able to move the drive block 16 in the arcuate channel 8 by virtue of the drive train, thereby moving the ultrasound transducer 6, which is mounted on the drive block 16. To record rotational position of a drive shaft of the motor 10, the motor 10 is equipped with an incremental encoder 18, whereby position information from the incremental encoder 18 is correlated to and used to determine position of the ultrasound transducer 6.

The main body 7 further comprises a start switch 21 (e.g., a button, toggle or the like) and limit sensors 22 (e.g., limit switches such as magnetic Hall effect sensors or simple toggle switches) (only one labeled), as well as a controller 20 in electronic communication with the motor 10, the incremental encoder 18, the start switch 21 and the limit sensors 22. The controller 20 may be a simple controller or a programmed logic controller (PLC). The controller 20 is responsible for starting and stopping the motor 10, and is therefore responsible for controlling the motion of the ultrasound transducer 6. The limit sensor 22 sends a signal to the controller 20 when the drive block 16 has moved to the extreme ends of its motion, which represents an end to a compound scan, so that the controller 20 can stop the motor 10.

In some embodiments, the ultrasound device 1 is powered and controlled over an electrical connection, for example a USB to Serial connection, with a computer. The computer is programmed with computer readable code (software) that defines instructions for moving the ultrasound transducer 6. The software issues motor move commands to the controller 20 from either a press of the start switch 21 or from features in the software. The controller 20 receives the commands and moves the motor 10 by a pre-determined amount. Using the incremental encoder 18, the controller 20 tracks speed and position of the drive block 16. The limit sensors 22 are used so that the controller 20 does not allow the ultrasound device 1 to operate outside of a safe travel distance.

A case 25 covers the main body 7, in particular electronic components of the actuator 5 including the motor 10, the incremental encoder 18, the limit sensor 22 and the controller 20. The start switch 21 protrudes through an aperture in the case 25 to be accessible to a user. The case is ergonomically designed with grooves and contours to fit comfortably in a user's hand with the start switch 21 readily accessible to at least one digit of the user's hand.

Figure 4C:
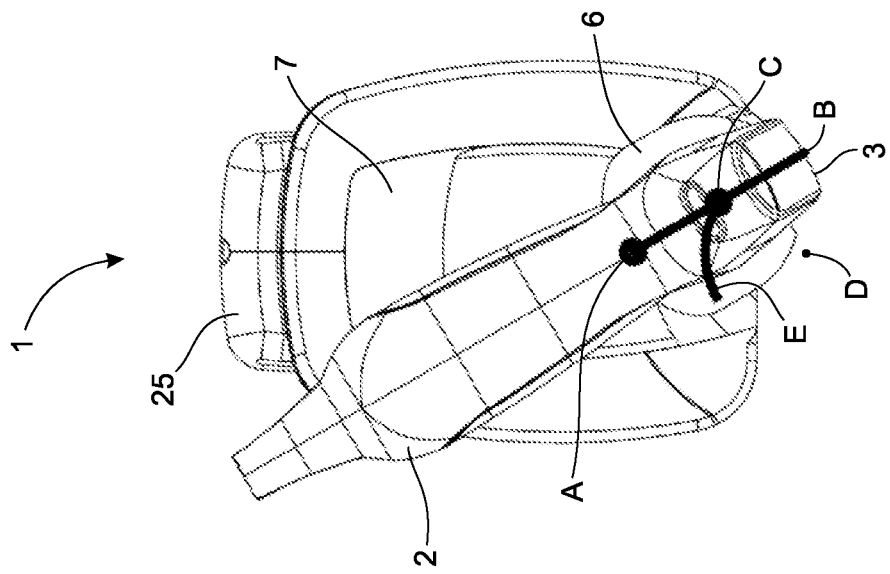
FIG. 4A, FIG. 4B and FIG. 4C depict three different positions that the ultrasound transducer of ultrasound device of FIG. 1A can acquire when moved by the actuator.
Figure 4B:
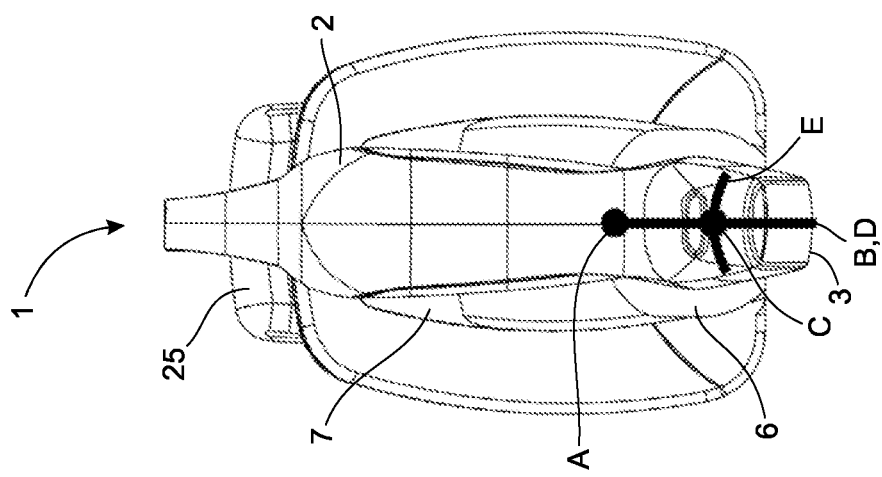
Figure 4A:
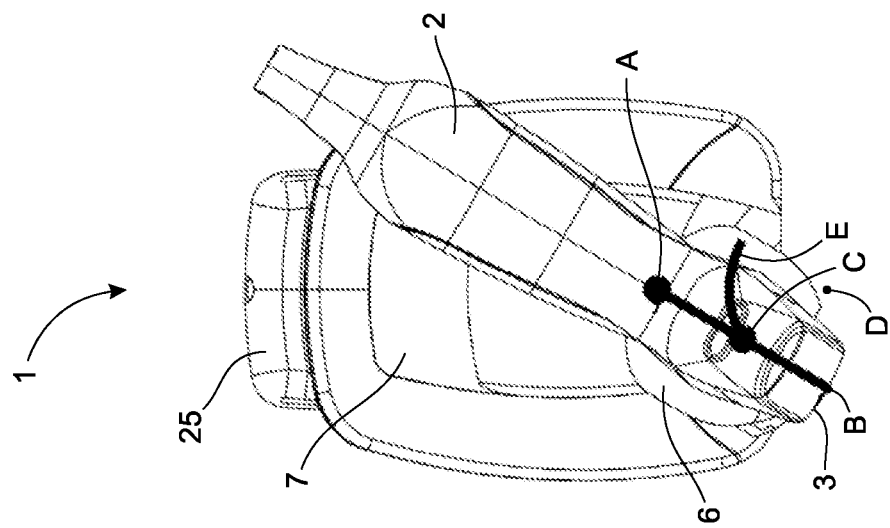
Figure 5C:
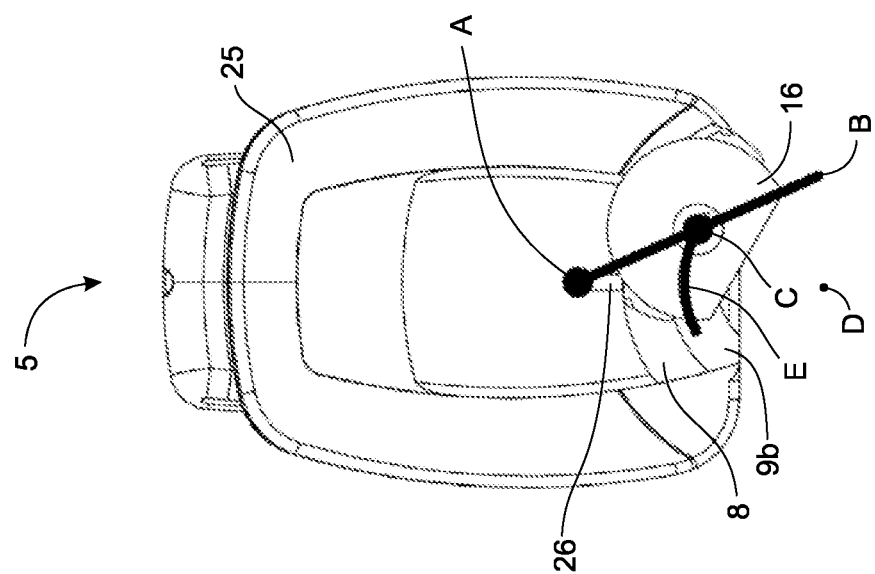
FIG. 5A, FIG. 5B and FIG. 5C depict positions of the drive block when the ultrasound transducer is in the positions illustrated in FIG. 4A, FIG. 4B and FIG. 4C, respectively.
Figure 5B:
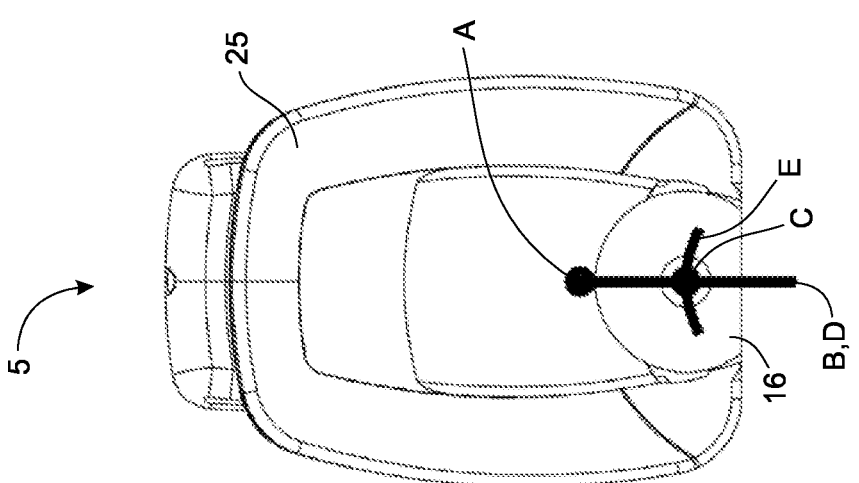
Figure 5A:
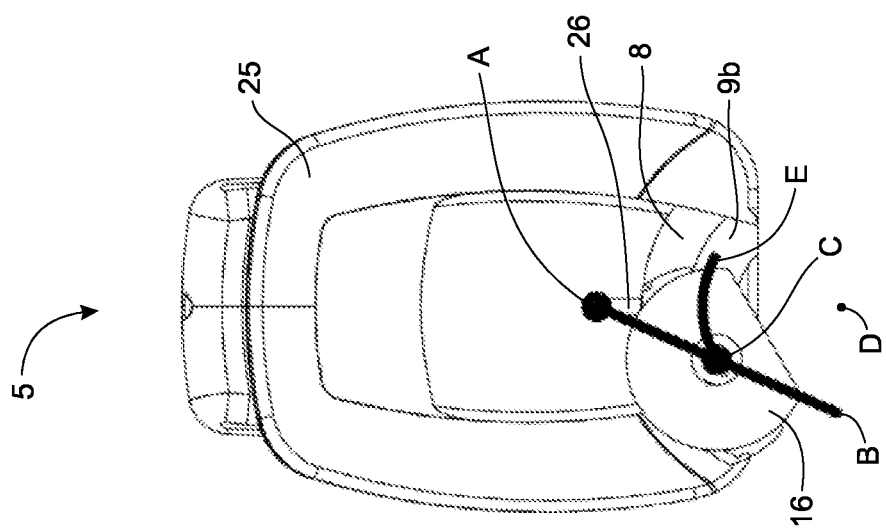

In operation, the ultrasound device 1 is carried in the hand of a user or on a robot arm to a site where an ultrasound scan will encompass the target region of interest. At that site, the ultrasound device 1 is held stationary while the compound scan is performed with the ultrasound device 1. To perform the compound scan, the ultrasound device 1 is actuated by sending a signal to the controller 20 using the start switch 21 or by some other electronic means such as from a computer in electronic communication with the controller 20. As seen in FIG. 4A to FIG. 4C, the compound scan involves sweeping a tip 3 of a head 2 of the ultrasound transducer 6 through an arc by rotating the ultrasound transducer 6, while also translating the ultrasound transducer 6 laterally with respect to the axis of rotation of the ultrasound transducer 6, which passes through pivot point C perpendicular to a line segment between points A and B, the pivot point C being at the midway point between points A and B. FIG. 4A to FIG. 4C show the range of motion of the ultrasound transducer 6, while FIG. 5A to FIG. 5C show the range of motion of the drive block 16 during the compound scan. FIG. 5A to FIG. 5C respectively correspond to FIG. 4A to FIG. 4C except that the ultrasound transducer 6 is removed in FIG. 5A to FIG. 5C. Point B is located at the tip 3 of the he ad 2 of the ultrasound transducer 6 where the ultrasound transducer 2 acquires ultrasound images of the target region. For use on humans or animals, the tip 3 is often coated with an ultrasound gel and in contact with skin during the compound scan. As the ultrasound device 1 is operated, 2D ultrasound images are continuously captured in the software to reconstruct a 3D ultrasound volume that can be used in diagnosis, treatment or therapy. After the full sweep of the tip 3 is complete (i.e., FIG. 4A through FIG. 4B to FIG. 4C, or vice-versa), the ultrasound device 1 is switched off and the ultrasound device 1 is moved to another site to scan another target region of interest.

As is seen FIG. 4A to FIG. 4C and FIG. 5A to FIG. 5C, the ultrasound transducer 6 and the drive block 16 not only rotate about the pivot point C to change the angle of the head 2 of the ultrasound transducer 6 relative to horizontal, but also translate horizontally along an arc E, which is part of a circle having a center point D. As seen in FIG. 4B, the center point D is coterminous with the point B at the tip 3 of the head 2 of the ultrasound transducer 6 when the head 2 of the ultrasound transducer 6 is vertically oriented. Thus, both the angular orientation and the lateral position of the ultrasound transducer 2 change during a compound scan. The consequences of this dual motion are discussed below with reference to FIG. 7A to FIG. 7C. The embodiment illustrated in FIG. 1A to FIG. 5C is designed to achieve a total linear translation of 42 mm of the tip 3 as the tip 3 sweeps through 60°. To achieve the 42 mm translation of the tip 3, line segment A-B must be equal to 42 mm. The pivot point C is midway between points A and B; therefore, the pivot point C is 21 mm from point B. If a different linear translation distance and sweep angle is desired, the pivot point C can be moved closer to or farther from point B, which is located at the tip 3 of the head 2 of the ultrasound transducer 6.

The pivot for pivot point C is machined as part of the drive block 16, while the main body 7 has the arcuate channel 8 machined therein to permit movable mounting of the curved guide slide 19 of the drive block 16. The main body 7 also has a linear slide 26 machined therein for linear constraint of point A. The receiver 4 of the ultrasound transducer 6 rotates about point C on the drive block 16 and has a pin 24 that is constrained in the linear slide 26 machined into the main body 7.

Figure 6D:
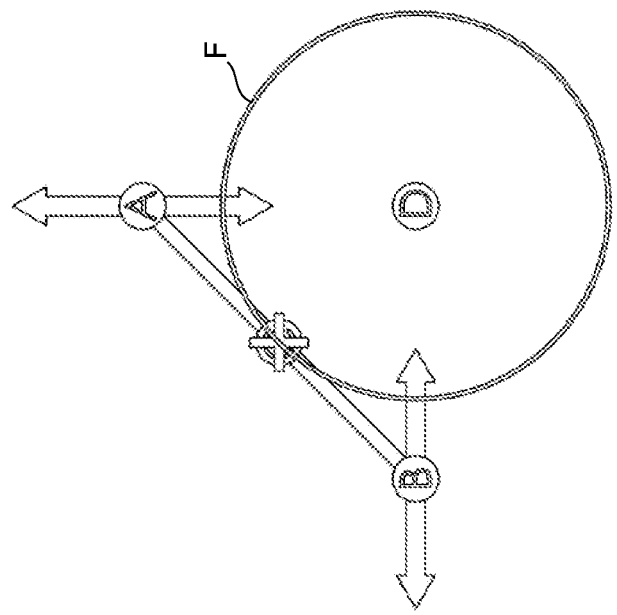
FIG. 6A, FIG. 6B, FIG. 6C and FIG. 6D schematically depict an Archimedes Trammel on which the motions of the ultrasound device are based.
Figures 6B, 6C:
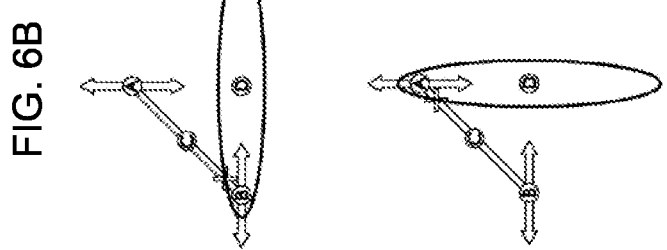
Figure 6A:
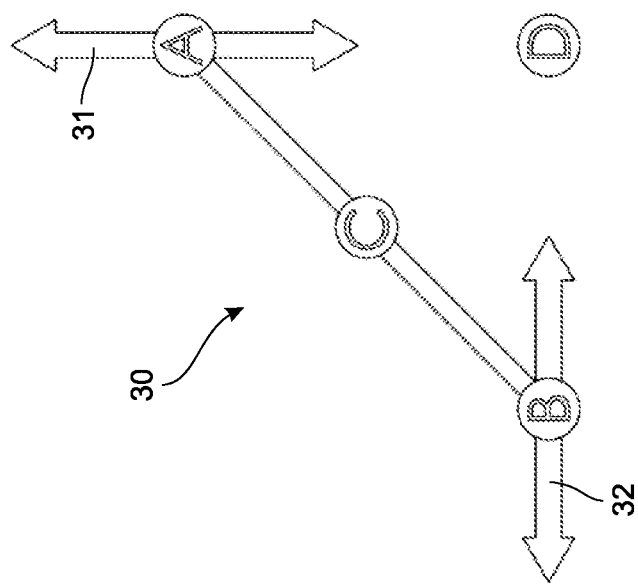

The ultrasound device 1 is based on a deconstructed Archimedes Trammel. An Archimedes Trammel 30, as schematically illustrated in FIG. 6A to FIG. 6D, has first and second linear slides 31, 32, respectively, which are perpendicular to each other and cross each other in the middle at point D. A pivot A is mounted on the first slide 31, and a pivot B is mounted on the second slide 32. A connecting link 33 between the pivots A, B on the two slides 31, 32 create line segment A-B finishing the trammel. As line segment A-B is rotated, pivot A slides vertically and pivot B slides horizontally. The Trammel 30 can be used to draw an ellipse by tracking a point along the line segment A-B. Depending on the location of the point being tracked, a variety of ellipses can be drawn with the major axis along the axis of either of the linear slides 31, 32, as shown in FIG. 6B and FIG. 6C. If the point being tracked is at a midpoint C between pivot A and pivot B, a circle F is drawn with center point D, as illustrated in FIG. 6D.

The ultrasound device 1 takes advantage of the arrangement illustrated in FIG. 6D, where the Archimedes Trammel can be used to draw a circle. Points A, B, C and D as labeled in FIG. 4A to FIG. 5C correspond to points A, B, C and D as labeled in FIG. 6A and FIG. 6D. The ultrasound device 1 constrains the pin 24 (point A) in the linear slide 26 vertically above point D, and point A is driven by moving point C along the arc E that has a radius of half of the length of line segment A-B and a center point at the intersection D of the two linear slides 31, 32, resulting in point B moving along a straight line.

The ultrasound transducer 6 is mounted on the line segment A-B so that the tip 3 of the ultrasound transducer 6 is at point B pointed away from point A. A Home position of the ultrasound device 1 has points A, B and C aligned vertically, where point B is coincident with point D. To reach a Scan Start position, point C is driven 30° along the arc E whose center is at point D, thereby moving the line segment A-B to a 30° angle from vertical and keeps point B aligned horizontally with point D. The distance between point B and point D is now half of line segment A-B. When point C is driven 60° in the other direction along the arc E, the ultrasound device 1 reaches a Scan End position. The ultrasound device 1 is then driven back to the Home position. Between the Scan Start position and the Scan End position the line segment A-B is continually rotating and point B is continually translating along a straight line. For each degree of rotation there is a linear increment of translation. The angle increment remains consistent throughout the rotation. The linear increment varies a small amount, gradually increasing up to 0.4% at 17° from vertical and then reducing back to 0% over the next 13° to 30° from vertical.

Figure 7C:
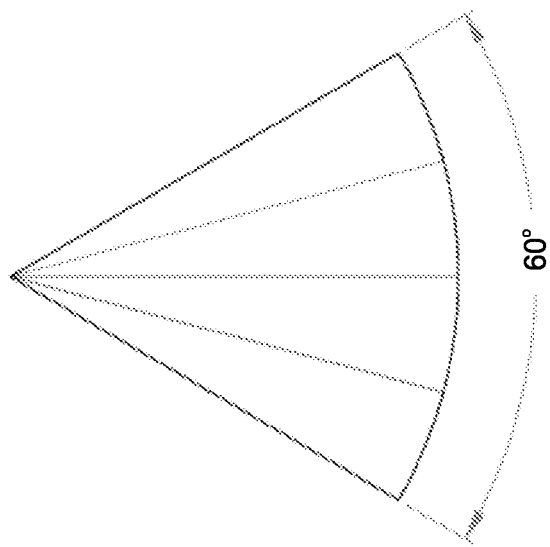
FIG. 7C depicts an image collection geometry acquired by an ultrasound transducer when the transducer is only rotated without being translated.
Figure 7B:
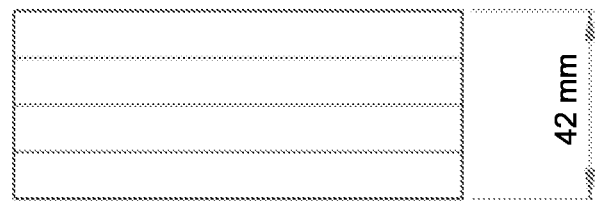
FIG. 7B depicts an image collection geometry acquired by an ultrasound transducer when the transducer is only translated without being rotated.
Figure 7A:
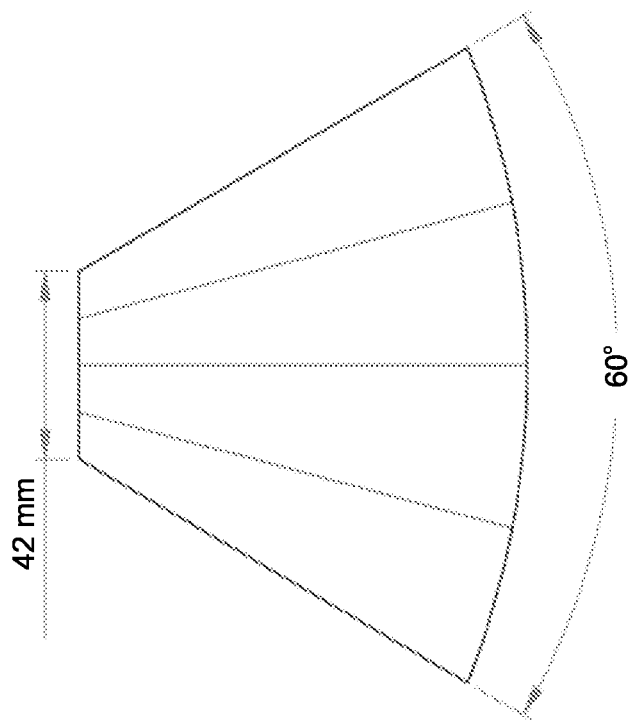
FIG. 7A depicts an image collection geometry acquired by an ultrasound transducer when the transducer is both translated and rotated by the actuator of the device of FIG. 1A.

With reference to FIG. 7A to FIG. 7C, the dual simultaneous motion (rotation and translation) of the ultrasound transducer 6 using the ultrasound device 1 permits creation of 3D ultrasound volumes using conventional 2D ultrasound images. FIG. 7C illustrates an image collection geometry (i.e., a tilt geometry) acquired by an ultrasound transducer when the transducer is only rotated through 60° without being translated, as is done in U.S. Pat. No. 5,562,095. FIG. 7B illustrates an image collection geometry (i.e., a linear geometry) acquired by an ultrasound transducer when the transducer is only translated through 42 mm without being rotated. FIG. 7A illustrates an image collection geometry (i.e., a hybrid geometry) acquired by an ultrasound transducer when the transducer is both translated 42 mm and rotated through 60°, as is done with the ultrasound device 1 and with the device in U.S. Pat. No. 10,052,083. However, the ultrasound device 1 is capable of acquiring ultrasound images in the hybrid geometry using only one motor, whereas the device of U.S. Pat. No. 10,052,083 requires two motors. The ultrasound device 1 simplifies operation and is more compact than the device of U.S. Pat. No. 10,052,083. The 2D images are combined and displayed as a 3D volume that provides better spatial awareness and situational context than 2D alone. By slicing through the 3D volume using the ultrasound device 1, other image planes can be displayed that cannot be acquired with conventional 2D ultrasound, for example an image at a specified depth parallel to the skin. The volume of the hybrid geometry is nearly equal to the linear and tilt geometries combined. Thus, the ultrasound device 1 is very useful for capturing large deep structures and for trajectory planning for deep targeting while avoiding shallow structures.

The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:

1. An actuator for moving an ultrasound transducer, the actuator comprising:
   a main body configured to be positioned adjacent to a target region of interest to be examined;
   a motor mounted on the main body, the motor configured to have the ultrasound transducer connected thereto to simultaneously translate and rotate the ultrasound transducer to perform a compound scan of the target region of interest when the ultrasound transducer is connected to the motor;
a drive block to which the ultrasound transducer is mounted, the drive block operatively connected to the motor to be rotationally and translationally moved by the motor;
the motor is operatively connected to a rotatable engagement structure that is rotationally driven by the motor; and,
the drive block comprises an arcuate engagement surface that is engaged with the rotatable engagement structure;
wherein rotation of the rotatable engagement structure drives the arcuate engagement surface thereby causing the drive block to both rotate with the rotatable engagement structure and translate laterally relative to a rotation axis of the rotatable engagement structure, and
wherein the main body comprises a linear slide and the ultrasound transducer comprises a receiver rotatably mounted on the drive block, the receiver having a pin that is constrained in the linear slide so that a tip of the ultrasound transducer translates linearly and laterally relative to the rotation axis of the rotatable engagement structure when the ultrasound transducer translates and rotates.

2. The actuator of claim 1, wherein the drive block rotates about a point that is a center of a circle of which the arcuate engagement surface is a part, the drive block translating along a perimeter of the circle.

3. The actuator of claim 2, wherein the rotatable engagement structure comprises a toothed gear and the arcuate engagement surface comprises a toothed track that engages with the toothed gear.

4. The actuator of claim 3, wherein the toothed gear is a pinion gear and the toothed rack is a segment of an internal ring gear.

5. The actuator of claim 1, wherein the main body comprises an arcuate channel; and, a portion of the drive block comprising the arcuate engagement surface has a complementary shape to the arcuate channel so that the portion of the drive block with the arcuate engagement surface can be housed in the arcuate channel while permitting the drive block to rotate and translate when driven by the motor.

6. An ultrasound device comprising the actuator of claim 1 and the ultrasound transducer connected to the motor of the actuator.

7. An actuator for moving an ultrasound transducer, the actuator comprising:
a main body configured to be positioned adjacent to a target region of interest to be examined; and,
a motor mounted on the main body, the motor configured to have the ultrasound transducer connected thereto to simultaneously linearly translate a tip of the ultrasound transducer and arcuately move a rotation point of the ultrasound transducer to perform a compound scan of the target region of interest when the ultrasound transducer is connected to the motor,
wherein the main body comprises a linear slide and the ultrasound transducer comprises a receiver, the receiver having a pin that is constrained in the linear slide so that the tip of the ultrasound transducer translates linearly when the ultrasound transducer translates and rotates.

8. The actuator of claim 7, wherein the actuator further comprises a drive block on which the ultrasound transducer is rotatably mounted through the receiver, the drive block operatively connected to the motor to be rotationally and translationally moved by the motor.

9. The actuator of claim 8, wherein:
the motor is operatively connected to a rotatable engagement structure that is rotationally driven by the motor; and,
the drive block comprises an arcuate engagement surface that is engaged with the rotatable engagement structure,
wherein rotation of the rotatable engagement structure drives the arcuate engagement surface thereby causing the drive block to both rotate with the rotatable engagement structure and translate laterally relative to a rotation axis of the rotatable engagement structure.

10. The actuator of claim 9, wherein the drive block rotates about a point that is a center of a circle of which the arcuate engagement surface is a part, the drive block translating along a perimeter of the circle.

11. The actuator of claim 9, wherein the rotatable engagement structure comprises a toothed gear and the arcuate engagement surface comprises a toothed track that engages with the toothed gear.

12. The actuator of claim 11, wherein the toothed gear is a pinion gear and the toothed rack is a segment of an internal ring gear.

13. The actuator of claim 9, wherein the main body comprises an arcuate channel; and, a portion of the drive block comprising the arcuate engagement surface has a complementary shape to the arcuate channel so that the portion of the drive block with the arcuate engagement surface can be housed in the arcuate channel while permitting the drive block to rotate and translate when driven by the motor.

14. The actuator of claim 8, further comprising an encoder for determining position of the drive block as the drive block rotates and translates.

15. The actuator of claim 7, further comprising a casing for the main body enclosing at least the motor.

16. The actuator of claim 7, further comprising a limit switch for stopping the motor at an end of the compound scan.

17. The actuator of claim 7, further comprising a user actuatable control on the main body to start the compound scan.

18. The actuator of claim 7, configured to be mounted on a robot arm and controlled by a programmed logic circuit.

19. An ultrasound device comprising the actuator of claim 7 and the ultrasound transducer connected to the motor of the actuator.

\* \* \* \* \*